(12) United States Patent
Kuo et al.

(10) Patent No.: US 9,775,920 B2
(45) Date of Patent: Oct. 3, 2017

(54) USE OF N-(4-ISOPROPYLPHENYL)-5-AMINO-ISOINDOLINE

(71) Applicant: Institute of Nuclear Energy Research, Atomic Energy Council, Executive Yuan, R.O.C., Taoyuan (TW)

(72) Inventors: Wan-I Kuo, Taoyuan (TW); Jian-Hua Zhao, Taoyuan (TW); Kang-Wei Chang, Taoyuan (TW); Tsai-Yueh Luo, Taoyuan (TW); Wei-Hsi Chen, Taoyuan (TW)

(73) Assignee: INSTITUTE OF NUCLEAR ENERGY RESEARCH, ATOMIC ENERGY COUNCIL, EXECUTIVE YUAN, R.O.C., Taoyuan (TW)

( * ) Notice: Subject to any disclaimer, the term of this patent is extended or adjusted under 35 U.S.C. 154(b) by 0 days.

(21) Appl. No.: 15/223,559

(22) Filed: Jul. 29, 2016

(65) Prior Publication Data
US 2017/0028087 A1   Feb. 2, 2017

(30) Foreign Application Priority Data
Jul. 31, 2015  (TW) .............................. 104124996 A

(51) Int. Cl.
A61K 51/00   (2006.01)
A61M 36/14   (2006.01)
A61K 51/04   (2006.01)

(52) U.S. Cl.
CPC ................................ *A61K 51/0446* (2013.01)

(58) Field of Classification Search
CPC .................................................... A61K 51/0446
USPC ......................................................... 424/1.81
See application file for complete search history.

(56) References Cited

U.S. PATENT DOCUMENTS 7,700,616 B2 *   4/2010   Tamagnan ......... A61K 31/4184
                                                        514/299

OTHER PUBLICATIONS

Lee et al. Bioorg. Med. Chem. Lett. 18 (2008) 1628-1631.*
Orit Jacobson et al., Fluorine-18 Radiochemistry, labeling Strategies and Synthetic Routes, Bioconjugate Chemistry, 2015, 1-18, 26.

* cited by examiner

*Primary Examiner* — Michael G Hartley
*Assistant Examiner* — Sean R Donohue
(74) *Attorney, Agent, or Firm* — Locke Lord LLP; Tim Tingkang Xia, Esq.

(57) ABSTRACT

The present invention relates to a novel use of N-(4-isopropylphenyl)-5-amino-isoindoline for diagnosing Alzheimer's disease and quantifying amyloid in the brain.

3 Claims, 1 Drawing Sheet

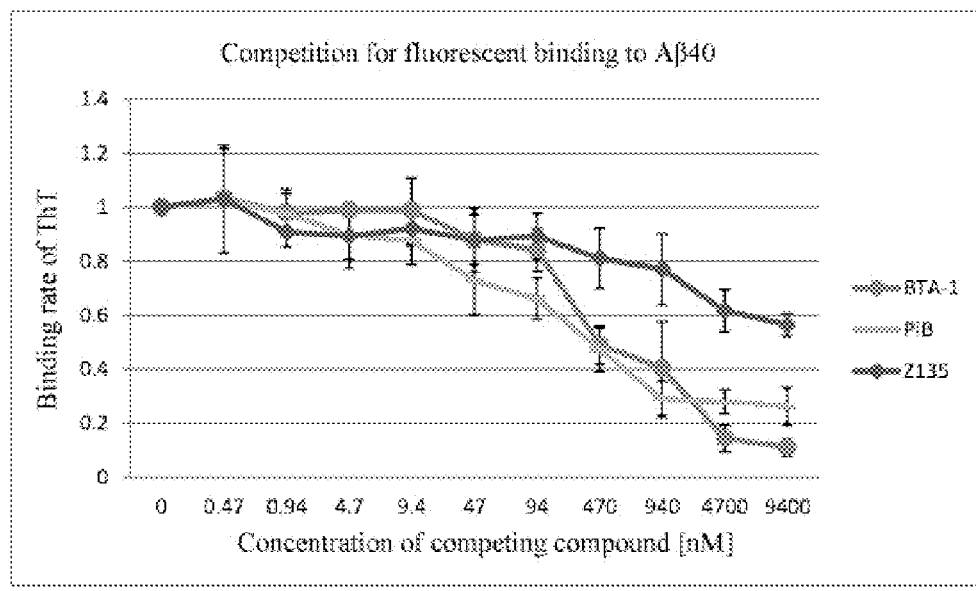

USE OF N-(4-ISOPROPYLPHENYL)-5-AMINO-ISOINDOLINE

CROSS REFERENCE TO RELATED APPLICATION

This application also claims priority to Taiwan Patent Application No. 104124996 filed in the Taiwan Patent Office on Jul. 31, 2015, the entire content of which is incorporated herein by reference.

TECHNICAL FIELD

The present disclosure relates to novel use of N-(4-isopropylphenyl)-5-amino-isoindoline for diagnosing Alzheimer's disease and quantifying amyloid in the brain.

BACKGROUND

Alzheimer's disease (AD) is a progressive and irreversible neurodegenerative disorder characterized by progressive cognitive deficiency or dysfunction and by early memory impairment of recent events. With the contemporary development of medical care and the increase in age of senile population, more economic and social costs are caused to be spent in the treatment or caring of patients with AD in the future. In the existing medical diagnostic techniques, neuropsychological assessment is frequently used for evaluation, including clinical measurements for evaluating the memory, lingual function, cognitive function, attention, and individual behaviors of AD patients. Such diagnostic methods lack the sensitivity and specificity for diseases, and are of limited significance for the treatment of patients, since the neuropathy in the brain is developed to a serious stage when the patients are detected to suffer from AD based on the assessment. Therefore, information about physiological functions may be provided by nuclear pharmaceutical agent in combination with positron emission tomography (PET) imaging, and the pathological status of the disease may be presented by nuclear imaging.

AD is characterized by progressive cognitive deficiency or dysfunction, and memory and executive dysfunction are accordingly the critical factors in early diagnosis in almost all the cases. However, the cerebral pathological changes originating from AD are present as early as ten to twenty years before the occurrence of cognitive decline or behavior change in the patients, and the pathological features are neurofibrillary tangles (NFTs) caused by seline plaques (SPs) of diffuse Aβ protein (β-amyloid), and hyperphosphorylated tau protein (Kung M P et al., 2004; Kulkarni P V et al, 2005). The tangles and plaques block the nerves from communication with each other and from signaling. The plaques are produced because the amyloid precursor protein (APP) cleavage enzyme cannot function properly, causing the β-cleavage enzyme and the γ-cleavage enzyme to alter the APP catabolic process, such that the beta amyloid is over produced (Routtenberg A et al, 1997). This type of protein is prone to aggregation, to form a precipitate, which may possibly lead to the beginning of neurodegeneration and decrease in secretion of neurotransmitter.

The formation of amyloid plaques is an early focus in development of AD, which occurs before cognitive impairment, memory difficulty, and symptoms as observed by FDG-positron emission tomography and MRI imaging, and earlier and more significant than the production of cerebrospinal fluid tau protein.

The most definitive diagnosis for AD is through Anatomy of the brain to observe pathological characteristics. Therefore, there is a need to determine whether the patients suffer from AD when alive by some molecular diagnostic techniques. In 2011, new diagnostic criteria and proposals are jointly published by National Institute on Aging (NIA) and Alzheimer's Association (AA), in which biomarkers are regarded as reference for inclusion in diagnostic criteria. The first class of diagnostic criteria include increased APβ protein deposition in the brain, decreased Aβ42 protein level in the cerebrospinal fluid, and positive reaction in the PET amyloid imaging. The second class of diagnostic criteria include persistently degenerated and injured nerve cells, including increased tau and phosphorylated tau (p-tau) protein level in the cerebrospinal fluid, weakened signal at the apical temporal lobe of the brain as shown by F-18 FDG-positron emission tomography, and particular atrophy at the temporal lobe and the inner apical lobe of the brain as shown by NMR imaging (see NTU Hospital Health Newsletter No. 73, December 2013). With the increasingly sophisticated nuclear imaging technology, if the early diagnosis of AD is available, treatment may be administered in the early stage of disease development, and the efficiency of the therapeutic agent in the clinical trial is increased. Also, the in-time diagnosis of the disease can allow their family members to have psychological preparation to give appropriate care, and reduce the discomfort of patients to improve the quality of life. Therefore, development of new drugs for AD is still a topic to which unremitting efforts are made by the scientists.

Abnormal accumulation of β-amyloid in the brain is believed to be the main cause of loss of memory in the patients. As such, some therapeutic agents under development target at this protein, and are expected to inhibit the undesirable production or reduce the undesirable accumulation of the protein. However, a bottleneck is encountered in the development of drugs for AD. That is, the patients with AD are diagnosed only after the clinical symptoms are displayed, and at this time, too much non recoverable damage is accumulated in the brain of the patients. Accordingly, it is necessary and urgent to develop an early diagnostic tool both in the study of the role of β-amyloid in AD and in the detection of the progression of AD.

In the past, in-vivo non-invasive study of glucose metabolism in the brain by using PET with F-18 FDG (2-deoxy-2-[F-18]fluoro-D-glucose) has a history of over 25 years (Nakamura S et al., 2001). It is found in the study using PET/F-18 FDG that in the AD patients, a clinical symptom of considerably reduced metabolism of F-18 FDG at the position of the focus is shown. The reduced absorption of F-18 FDG occurs even ahead of the cognitive dysfunction, and is positively correlated with the severity of dementia. Although F-18 FDG provides some interpretations with respect to metabolism, these interpretations cannot indicate the specific position of the lesion in the brain (Lee C W et al., 2003) or are not specific function tests for AD patients (Ye L et al., 2006).

In recent years, the nuclear pharmaceuticals and positron emission tomography (PET) imaging are developed remarkably. The contrast agent C-11 PiB (Pittsburgh Compound B) having a high affinity to β-amyloid is specifically used in the detection of β-amyloid, or the deposition of β-amyloid may be quantified by imaging. However, the half-life of C-11 is only 20 min, and the produced agent cannot be shipped to other hospitals for use, is limited to entities having cyclotron, and cannot be commercialized. Therefore, to seek a more stable and specific contrast agent, F-18 tagged PiB (Flutemetamol, GE Healthcare), F-18-AV-45 (Florbetapir, AVID-RP/Lilly) and F-18-AV-1 (Florbetaben, Piramal) enter clinical trial in succession. The F-18 has a half-lie of up to 110 min, a high energy, and a good sensitivity, and can be shipped. In addition, the contrast agent for dementia under development at present further includes Azd4694 (Navidea). These contrast agents all suffer from some drawbacks, for example, some sub-regions cannot be detected, the specificity remains to be tested and there is no consistent determination standards for clinical diagnosis. Moreover, considering the patent right, the clinical trial can be conducted at home only at the allowance of the above enterprises and by purchase from the manufacturer. The royalty payment is enormous over a long period of time, resulting in a high imaging cost, and the imaging cannot be a routine test. Domestic research and development of the contrast agent is more cost-effective and conducive to the improvement of the caring quality of the patients.

In view of the foregoing, by screening by computer simulation and validating the ability of compounds to bind to amyloid through in-vitro binding ability assay, the N-(4-isopropylphenyl)-5-amino-isoindoline is screened out, which can be used for detection of AD in-vivo. In this way, the present invention is accomplished.

SUMMARY

The present invention relates to use of N-(4-isopropylphenyl)-5-amino-isoindoline represented by Formula (1) below for diagnosing Alzheimer's disease and quantifying amyloid in brain.

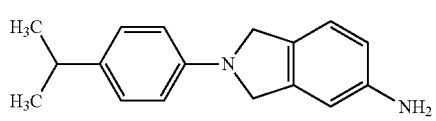

(1)

The N-(4-isopropylphenyl)-5-amino-isoindoline of the present invention is a known compound (see zinc.docking.gov) that is commercially available, and the synthesis of which is not described again.

The inventors find through in-vitro assay of N-(4-isopropylphenyl)-5-amino-isoindoline (referred to as "the compound of the present invention") that the compound can compete with the β-amyloid dye thioflavin T (ThT) for binding to amyloid, suggesting that the compound of the present invention has the ability to bind to amyloid.

Furthermore, the compound of the present invention has a molecular weight that is lower than 500 and a liposolubility that is higher than 2, and is neutrally discharged, thus being capable of penetrating the blood brain barrier to enter the brain (the small molecular weight, electric neutrality, and high liposolubility allow the easy penetration of the blood brain barrier), and being useful for diagnosing AD and quantifying amyloid in the brain.

Particularly, due to the abilities to penetrate the blood brain barrier to enter the brain and to bind to amyloid, the compound of the present invention is presumed to be useful for diagnosing AD and quantifying amyloid in the brain when further marked with a suitable radioactive isotope.

The radioactive isotope useful for marking the compound of the present invention is not particularly limited as long as it is an isotope having radioactivity, for example, C-11 or F-18.

BRIEF DESCRIPTION OF DRAWINGS

FIG. 1 shows the result of the compound of the present invention competing with the amyloid florescent dye ThT for binding to Aβ40 in the example.

DETAILED DESCRIPTION OF DISCLOSED EMBODIMENTS

The N-(4-isopropylphenyl)-5-amino-isoindoline in the present invention (referred to as "the compound of the present invention" sometime) is screened out for its ability to bind to β-amyloid by molecular docking, binding pattern simulation, and in-vitro binding assay. The screening method is detailed now.

Structure-based drug design plays a very important role in the development of drugs. During the exertion of a drug efficacy, the drug molecule needs to be adequately close to the target, assumes a suitable orientation, and interacts with the target by appropriately adjusting the conformation, to form a stable complex. The structure-based drug design is achieved mainly by molecular docking. Molecular docking is one of the important molecular simulation methods, by which the interaction between the ligand and the receptor can be simulated according to the lock and key principle underlying the interaction between the ligand and receptor. The molecular recognition process involves hydrogen bonding, electrostatic interaction, hydrophobic interaction and van der Waals force. The binding pattern and affinity therebetween are predicted by computer simulation, to carry out the screening of virtual drugs. The two critical factors in molecular docking are intermolecular spatial and energy complementary, wherein the spatial identification is the intermolecular geometrical pairing, to seek the best interaction pattern between the ligand and the receptor, and the energy identification is used for evaluating the binding stability. Molecular docking is widely used for searching small molecules that have a good affinity to the receptor from a small molecule database, and then the small molecules are subjected to pharmacological test, to screen out potential lead compounds.

The software for screening the drugs is Discovery Studio 3.0 (Accelrys Inc., USA), in which the orientation of binding of the small molecular compound to the β-amyloid receptor is simulated by using the molecular docking CDOCKER module, and the CDOCKER uses a CHARMm-based docking technique and a pattern in which the receptor adopts a fixed conformation and the ligand adopts a flexible conformation, to evaluate the most stable orientation of binding. The compound of the present invention is screened out by (1) molecular docking; and (2) analysis of orientation of binding. After the compound of the present invention is screened out, the ability of the compound to bind to the β-amyloid receptor is confirmed by in-vitro binding assay.

The screening is performed by computer software and thus is not detailed in the present invention.

The method for assaying the ability of the compound of the present invention to bind to β-amyloid receptor is described by way of example below. However, the example is provided merely for illustrating, instead of limiting the scope of the present invention.

EXAMPLE

In-vitro Assay
Competition for fluorescent binding to Aβ40: the inhibition test of competition binding to amyloid was carried out, in which 2 μM Aβ40, 1 μM amyloid fluorescent dye ThT, and 0.47 nM, 0.94 nM, 4.7 nM, 9.4 nM, 47 nM, 94 nM, 470 nM, 940 nM, 4700 nM and 9400 nM of standard compounds (PiB and BTA-1) and the compound of the present invention as the competing compounds were used. The reaction was carried out for 2 hrs at room temperature, which was excited by using Anthos Zenyth 3100 at an excitation wavelength of 485 nm, and then emitted a florescence of 535 nm. The binding rate of ThT to amyloid was set to 1 where no compound of the present invention was added to compete with ThT for binding. The PiB and BTA-1 were used as positive controls, and the binding rate of each concentration of compound was calculated according to the formula: binding rate=(fluorescence intensity with the compound of the present invention/fluorescence intensity without the compound of the present invention). The result is shown in FIG. 1, in which the horizontal axis is the concentration of the competing compound, and the longitudinal axis is the binding rate of ThT. It can be known from the result shown in the figure that when the concentration of the competing compound is gradually increased, the binding rate of the fluorescent dye ThT is observed to decrease gradually with the increasing concentration of the compound of the present invention, which means that the fluorescent dye ThT binding to amyloid is replaced such that the fluorescence intensity is lowered, demonstrating that the compound of the present invention can well bind to β-amyloid. Also, it can be known from FIG. 1 that compared with PiB and BTA-1 known to have high affinity to β-amyloid, the compound of the present invention has a ThT binding rate comparable to that of other known compounds at a low concentration.

It can be known from the result above that due to the ability to well bind to β-amyloid, the compound of the present invention is anticipated to be one of the tools for detecting AD in vivo that is useful for diagnosing Alzheimer's disease and quantifying amyloid in the brain, thus being of great significance in medical industry.

What is claimed is:

1. A method of diagnosing Alzheimer's disease using a tissue sample from a subject comprising:
    contacting the tissue sample with a compound labelled with a radioactive element to detect an amyloid in the sample, wherein the compound is represented by Formula (1) below:

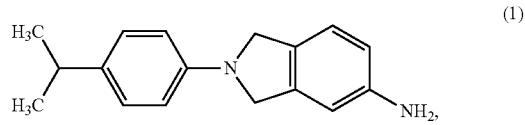 [SMILES: CC(C)c1ccc(N2Cc3ccc(N)cc3C2)cc1]

(1)

and
detecting the compound bound to the tissue sample.

2. The method according to claim 1, further comprising quantifying the amount of amylold in the tissue sample.

3. The method according to claim 1, wherein the radioactive element is C-11 or F-18.

* * * * *